US012608796B2

(12) United States Patent
Al-Ali

(10) Patent No.: US 12,608,796 B2
(45) Date of Patent: Apr. 21, 2026

(54) METHOD FOR CAPILLARY INDEX SCORING

(71) Applicant: Firas Al-Ali, Hudson, OH (US)

(72) Inventor: Firas Al-Ali, Hudson, OH (US)

(73) Assignee: E.CIS, LLC, Akron, OH (US)

( * ) Notice: Subject to any disclaimer, the term of this patent is extended or adjusted under 35 U.S.C. 154(b) by 328 days.

(21) Appl. No.: 18/141,745

(22) Filed: May 1, 2023

(65) Prior Publication Data

US 2024/0370994 A1     Nov. 7, 2024

(51) Int. Cl.
| | |
|---|---|
| *G06T 7/00* | (2017.01) |
| *A61B 6/00* | (2006.01) |
| *A61B 6/50* | (2024.01) |
| *G06T 7/12* | (2017.01) |

(52) U.S. Cl.
CPC ............ *G06T 7/0012* (2013.01); *A61B 6/481* (2013.01); *A61B 6/501* (2013.01); *A61B 6/504* (2013.01); *A61B 6/5217* (2013.01); *G06T 7/12* (2017.01); *G06T 2207/10116* (2013.01); *G06T 2207/20081* (2013.01); *G06T 2207/30016* (2013.01); *G06T 2207/30101* (2013.01)

(58) Field of Classification Search
CPC ..................... G06T 7/0012; G06T 7/12; G06T 2207/10116; G06T 2207/20081; G06T 2207/30016; G06T 2207/30101; G06T 2207/20084; A61B 6/481; A61B 6/501; A61B 6/504; A61B 6/5217
See application file for complete search history.

(56) References Cited

U.S. PATENT DOCUMENTS

| | | | |
|---|---|---|---|
| 9,486,176 | B2 | 11/2016 | Goyal |
| 10,898,152 | B1 | 1/2021 | Kim et al. |
| 11,532,144 | B2 | 12/2022 | Mueller et al. |
| 11,576,619 | B2 | 2/2023 | McLaughlin |
| 11,576,626 | B2 | 2/2023 | Fonte et al. |
| 11,602,322 | B2 | 3/2023 | Kim et al. |
| 2011/0257545 | A1 | 10/2011 | Suri |
| 2021/0209757 | A1 | 7/2021 | Min et al. |
| 2021/0236080 | A1 | 8/2021 | Herrmann et al. |
| 2023/0000364 | A1 | 1/2023 | Ionita |

OTHER PUBLICATIONS

Al-Ali et al.: "The Capillary Index Score in IMS I, II Trials"; Jul. 2014; NIH Public Access; Stroke (Year: 2014).*

(Continued)

*Primary Examiner* — Siamak Harandi

(74) *Attorney, Agent, or Firm* — Dominic A. Frisina

(57) ABSTRACT

An electronic capillary index scoring (eCIS) method is provided. The method includes providing a co-registered diagnostic cerebral angiogram (DCA) and quantifying an actual capillary blush area of a portion of the diagnostic cerebral angiogram representing an ischemic hemisphere. The method further quantifies an expected capillary blush area of the portion of the diagnostic cerebral angiogram representing the ischemic hemisphere. An eCIS is calculated by dividing the quantified actual capillary blush area by the quantified expected capillary blush area.

20 Claims, 13 Drawing Sheets

700

(56) References Cited

OTHER PUBLICATIONS

Jagani et al.: "Capillary Index Score and Correlation with Outcomes in Acute Ischemic Stroke: a Meta-analysis"; Jan. 2017; Journal of Vascular and Interventional Neurology; vol. 9, No. 3, pp. 7-13. (Year: 017).*

Al-Ali et al.: "Acute Ischemic Stroke Treatment, Part 2: "Treatment Roles of Capillary Index Score, Revascularization and Time"; Jun. 2015; Frontiers in Neurology"; vol. 6, Article 117 (Year: 2015).*

Firas, et al., Capillary Index Score in the Interventional Management of Stroke Trials I and II, AHA Journal. Jul. 2014. DOI: 10.1161/STROKEAHA.114.005304. Akron, Ohio. http://ahajournals. org by on Feb. 13, 2023.

* cited by examiner

100

400

500

600

700

701

800

1000

1100

1200

1300

METHOD FOR CAPILLARY INDEX SCORING

I. BACKGROUND OF THE INVENTION

A. Field of Invention

The invention generally relates to the field of medical imaging analysis methods.

B. Description of the Related Art

Diagnostic cerebral angiograms (DCAs) are widely used to assess acute ischemic stroke patients prior to thrombectomy and is the only way to access the occluded artery and remove the obstructing clot. A DCA is a type of two-dimensional x-ray projection image. Generally, the patient is injected with a contrast dye, allowing for visualization of the brain's vasculature by x-ray angiography. A frontal view of a diagnostic cerebral angiogram 100 is shown in FIG. 1. Certain landmarks are readily visible including the orbits of the eyes 102, and the brain vasculature 101. This procedure allows the surgeon to localize a blockage or aneurism.

When a blockage occurs, the brain tissue directly fed by the blocked artery can become ischemic, and if the ischemia persists for a long enough time it can result in cell death i.e., infarction. It is known that in some patients the cerebral arteries are connected to each other such, that if one blood vessel is occluded, the area that is usually fed by it can receive retrograde blood from another. Such connections are made from two set of arteries: Circle of Willis, and Pial collaterals. Collateral blood flow may not be sufficient to preserve tissue viability indefinitely, but it can be sufficient to buy the patient time for an intervention. Whether or not a tissue receives such collateral blood flow is highly dependent on the position of the blockage, and the individual patient.

The capillary index score (CIS) is an angiographic method to assess the extent of the collateral supply (through Circle of Willis and Pial collaterals) and to assess the initial infarction area in the ischemic hemisphere. The CIS is based on two related concepts. First, the area displaying capillary blush represents either normal or viable ischemic cerebral tissue. Second, the area lacking capillary blush represents infarcted, or dead, tissue and provides an estimation of the infarcted area. Knowing the amount of infarcted tissue allows the surgeon to make an informed judgment regarding treatment prognosis.

The CIS method was developed as a simple metric to identify patients with acute ischemic stroke who have sufficient collateral blood flow to allow for a good outcome after revascularization. The method roughly quantifies the amount of infarcted cerebral tissue in the territory fed by the middle cerebral artery, which has prognostic value. An example 200 of the CIS method is shown in FIG. 2. FIG. 2 shows two such angiograms, A and B, side-by-side. Angiogram A is a healthy brain (or possibly an ischemic brain without infarction), while Angiogram B is infarcted, the whole middle cerebral artery territory clearly lacking capillary blush. The surgeon analyzes the diagnostic cerebral angiogram by dividing the middle cerebral artery territory into three roughly equal sections and scoring each section, where a "1" indicates the presence of capillary blush, and a "0" indicates the absence of capillary blush. The sum of the scores is the CIS score. Thus, the healthy brain in Angiogram A has a CIS score of 3, and the heavily infarcted brain shown in Angiogram B has a CIS score of 0. A score of 2 or 3 suggests that intervention (e.g. thrombectomy) is likely to produce a favorable outcome, and a score less than 2 suggests that the intervention has a significantly lower chance of producing a good outcome.

Clearly, the CIS method is a course indicator having only four possible integer values 0 through 3. A more granular method may identify patients that are likely to benefit from intervention despite having a CIS score of 1, and may find a threshold beyond which thrombectomy is futile or even harmful. Such a method might ultimately lead to an acceptable selection criteria for thrombectomy, which is currently lacking. Some embodiments of the present invention may provide one or more benefits or advantages over the prior art.

II. SUMMARY OF THE INVENTION

Some embodiments may relate to a capillary index scoring method. One step comprises providing a co-registered diagnostic cerebral angiogram in frontal view or lateral view. A second step comprises quantifying an actual capillary blush area of a portion of the diagnostic cerebral angiogram representing an ischemic hemisphere. A third step comprises quantifying an expected capillary blush area of the portion of the diagnostic cerebral angiogram representing the ischemic hemisphere. And, a fourth step comprises dividing the quantified actual capillary blush area by the quantified expected capillary blush area.

Embodiments are also directed to variations on the step of quantifying an expected capillary blush area of an ischemic hemisphere as will be described in detail herein.

Embodiments apply to frontal and to lateral diagnostic cerebral angiogram views.

Some embodiments may be carried out manually or semi-manually, while others may be carried out by a suitably trained artificial intelligence data model as described in detail herein. A semi-manual method according to one embodiment includes manually identifying and demarcating the boundaries of areas used to calculate an electronic capillary index score, as described herein, and then using a computer to calculate the area within the boundaries.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein.

IV. DETAILED DESCRIPTION OF THE INVENTION

Figure 1:
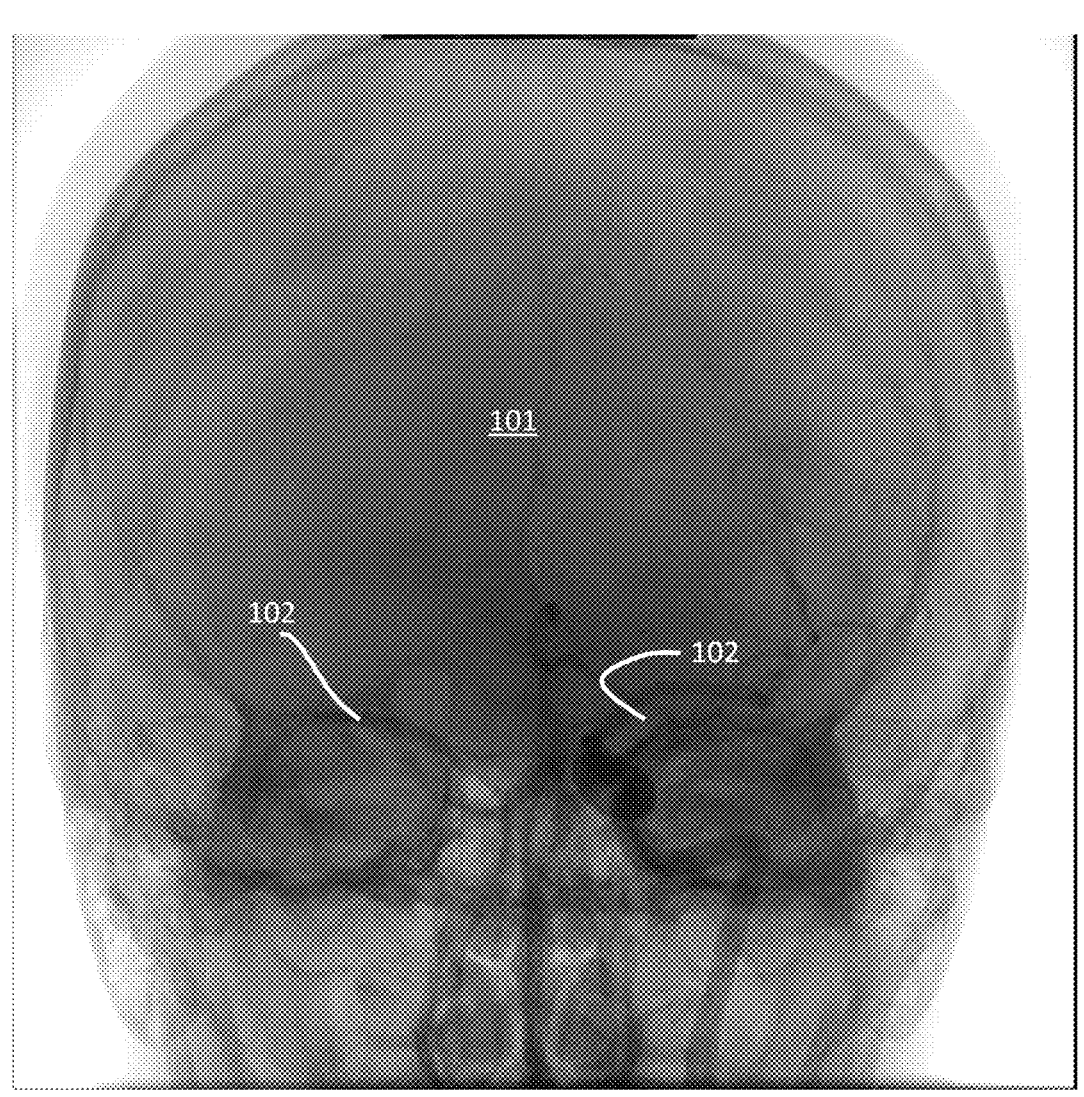
FIG. 1 is an example of an x-ray image in frontal view.
Figure 2:
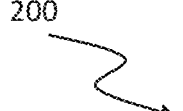
FIG. 2 is an example of a known CIS method.
Figure 2:
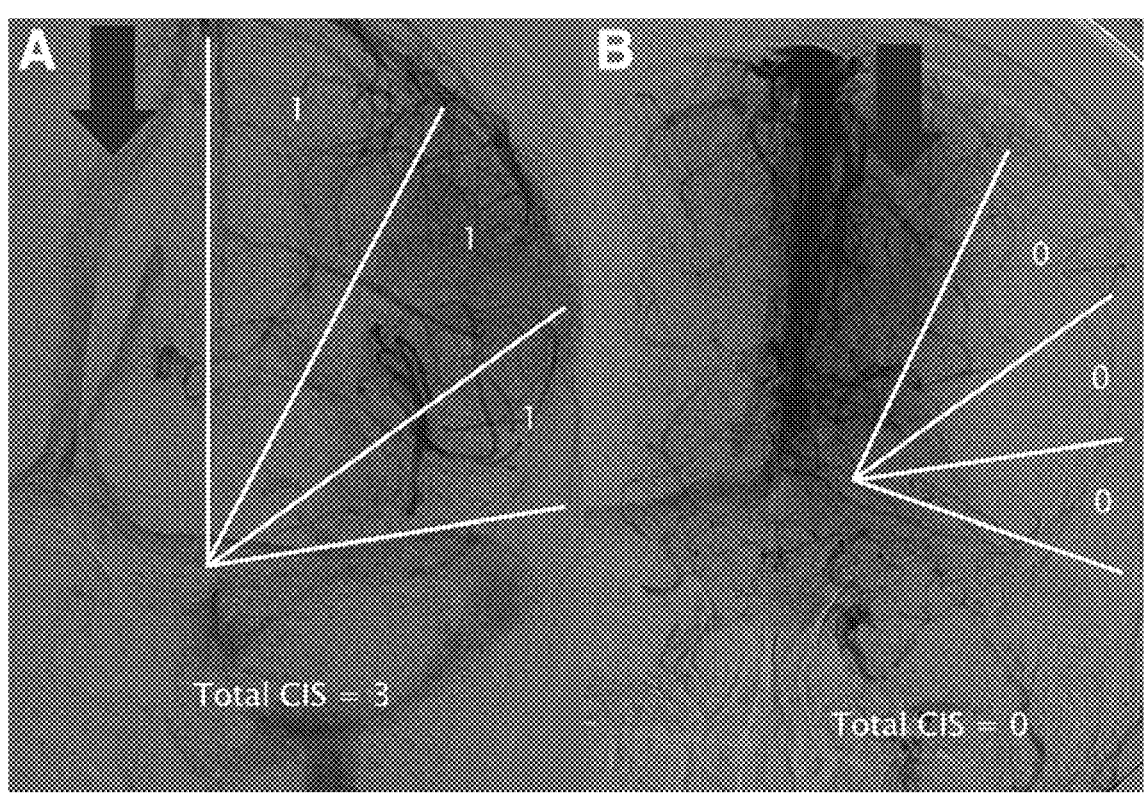

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

Terms of degree, terms of approximation, and/or subjective terms may be used herein to describe certain features or elements of the invention. In each case sufficient disclosure is provided to inform the person having ordinary skill in the art in accordance with the written description requirement and the definiteness requirement of 35 U.S.C. 112.

As used herein the term co-registered means an alignment or comparison of the blush and ischemic areas of three DCA images, such that blush and ischemic areas are identified and quantified in the ischemic and non-ischemic hemispheres, without counting blush areas more than once. The object of co-registration is to account for collateral blood flow to regions that would falsely appear ischemic if only direct blood flow was imaged. For example, three images may be co-registered as follows. In a first image, contrast dye is injected in a carotid artery feeding the ischemic hemisphere. In a second image, a contrast dye is injected in a carotid artery feeding the non-ischemic hemisphere. And in a third image, a contrast dye is injected in a vertebral artery feeding a posterior portion of the brain. In one embodiment, the first second and third injections can be made in any order, and still images may be captured, overlaid, and aligned i.e., co-registered. Additionally, the person having ordinary skill in the art will understand that more than one vertebral artery may be available for injection. Accordingly, if injecting one vertebral artery provides unsatisfactory results, failing to opacify the posterior fossa, another vertebral artery may be injected and may provide better results.

In another embodiment, the results of each of the three injections may be interpreted in real time on a live fluoroscopic image. For instance, the surgeon may make the first injection and note the blush and/or ischemic areas on a live fluoroscopic image in real time. The second injection may then be made and the blush and/or ischemic areas may be similarly noted. Finally, the third injection may be made, and the blush/ischemic areas may be noted. The process of comparing the blush and ischemic area results of each injection, is referred to as co-registration. Accordingly, co-registration allows the surgeon to conclude that any brain tissue lacking capillary blush is infarcted.

As used herein the phrase capturing a "co-registered two-dimensional x-ray projection image", according to the methods of the invention, includes capturing an individual image containing all co-registration data, and also includes capturing a plurality of images that are then overlaid, aligned, or otherwise compared to ensure that capillary blush areas are quantified only once.

In addition to frontal views, the methods described herein may also be performed on DCA lateral views. A lateral view may be indicated where the occlusion is in the M1, M2, or M3 segment of the middle cerebral artery (MCA), and the patient has a good A1 segment of the anterior cerebral artery (ACA).

As used herein the term "ischemic hemisphere" means the hemisphere of the brain having a large vessel occlusion and clinical symptoms.

Embodiments of the invention comprise a method for electronic capillary index scoring, also referred to herein as electronic CIS or eCIS, using diagnostic cerebral angiography (DCA) to determine the percentage of infarcted cerebral tissue in an ischemic hemisphere compared to an expected capillary blush area in the same hemisphere. The imaging data upon which scoring is performed is a 2D projection image of the brain taken in a frontal view, or a lateral view. The data is obtained by injecting a known contrast dye into the carotid artery branches feeding both the ischemic and non-ischemic hemispheres as well as the vertebral artery feeding the posterior portion of the brain. Injecting all three arteries co-registers all areas of the ischemic hemisphere receiving blood flow, regardless of whether the flow is direct or collateral. The areas of the brain image displaying no capillary blush are deemed to be infarcted.

According to various embodiments, one or more of the following surface area quantities may be calculated from the 2D DCA image: (i) the capillary blush surface area of the non-ischemic hemisphere, (ii) the bony landmark (the inside of the skull section) enclosing the non-ischemic hemisphere, (iii) the bony landmark enclosing the ischemic hemisphere, and (iv) the capillary blush surface area of the ischemic hemisphere. The ratio of the areas (ii:i) of the non-ischemic hemisphere and the section of skull enclosing it provides a constant C for calculating the expected capillary blush area of the ischemic hemisphere. According to this method, it is assumed that the ratio of areas of the non-ischemic hemisphere and the section of skull enclosing the non-ischemic hemisphere, is roughly equal to that of the ischemic hemisphere and the section of skull enclosing it. That is, any difference between the two ratios is assumed to be negligible.

$$C = \frac{A_{nonischemic\ bony\ landmark}}{A_{nonischemic\ hemisphere}} \qquad \text{Eq. 1}$$

More specifically, the constant C is divided into the area of the bony landmark ($A_{ischemic\ bony\ landmark}$) enclosing the ischemic hemisphere resulting in the expected capillary blush area ($A_{Expected}$)

$$A_{Expected} = \frac{A_{ischemic\ bony\ landmark}}{C} \qquad \text{Eq. 2}$$

The blush area ($A_{ischemic}$) of the ischemic hemisphere is divided by the expected blush area ($A_{Expected}$), which provides the percentage of infarcted cerebral tissue in the ischemic hemisphere. This percentage is termed the electronic capillary index score (eCIS).

$$eCIS = \frac{A_{ischemic}}{A_{Expected}} \qquad \text{Eq. 3}$$

One embodiment of the invention is a supervised learning method of training an artificial intelligence (AI) data model to identify healthy and ischemic brain tissue, as well as certain anatomical structures, and determine their areas for use in Equations 1 through 3. Accordingly, angiography data of healthy and ischemic brains are obtained and digitized in gray scale. The images may be labeled indicating areas having capillary blush, infarcted areas having no capillary blush, and may further include certain anatomical structures as will be described in further detail herein. The labeling comprises drawing an outline around the respective areas. The algorithm thus learns to recognize infarcted areas of an angiogram. The AI is similarly trained to recognize the outline of brain hemispheres and that of the bony landmarks. The trained algorithm is capable of recognizing the features involved in an eCIS calculation and computing their areas. The person having ordinary skill in the art will understand that the AI data model may also calculate an eCIS score, or the eCIS score may be computed according to other known means not involving artificial intelligence.

Figure 3:
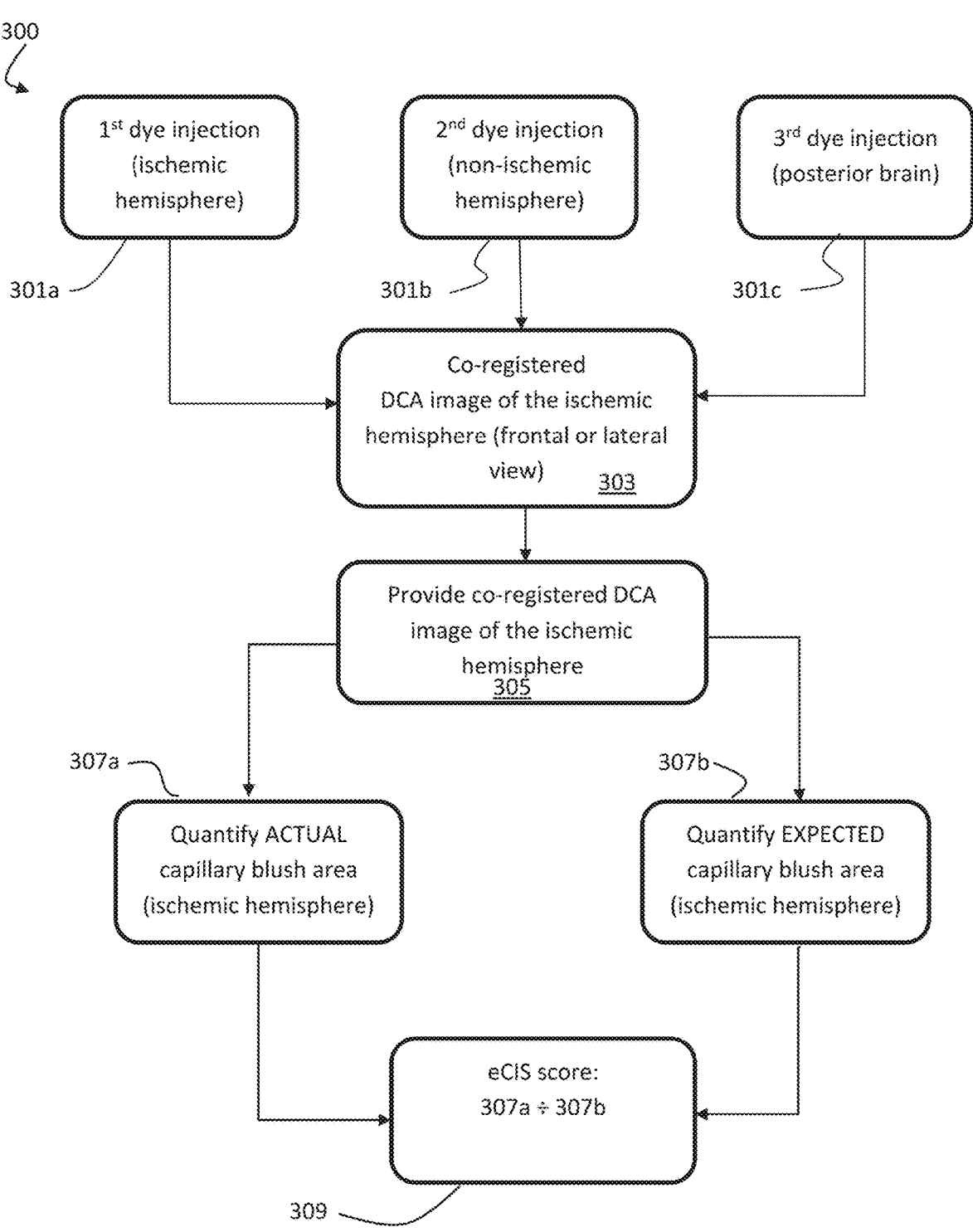
FIG. 3 is a diagram showing a generalized method for carrying out embodiments of the invention.

An example 300 of a method embodiment of the invention is shown in FIG. 3. This example includes dye injection steps 301a, 301b, and 301c. In step 301a the carotid artery branch feeding the ischemic hemisphere is injected with an x-ray opaque contrast dye. In step 301b the carotid branch feeding the non-ischemic hemisphere is similarly injected. And, in step 301c, a vertebral artery feeding the posterior portion of the brain is injected. Together, these three injections ensure that all brain tissue receiving direct and/or collateral blood flows will exhibit a visible capillary blush, meaning the resulting DCA of the ischemic hemisphere is co-registered 303. The person having ordinary skill in the art will understand that there is more than one methodology for producing a co-registered DCA. For instance, and without limitation, the three injections can be administered in any order as a matter of preference, or even simultaneously. The specific arteries selected for injection, and even the number of arteries, may differ from one method to another while still producing a co-registered DCA of the ischemic hemisphere. Any of a variety of well-known contrast dyes can be used according to the surgeon or radiologist's professional judgment.

Next the co-registered DCA is provided 305 for analysis. In some embodiments the analysis may be made by a suitably trained artificial intelligence data model, but in other embodiments the AI can be replaced with human intelligence. Accordingly, the act of providing can comprise a visual inspection by the surgeon, or the act of providing can be executed according to known machine vision methods. In step 307a the area of capillary blush shown in the DCA of the ischemic hemisphere is recognized and quantified. In step 307b a reference is established, namely, the expected capillary blush area of the ischemic hemisphere. As will be described in more detail herein, this step 307b can be carried out according to several alternative methodologies, all of which are embodiments of the invention. The electronic CIS (eCIS) 309 is the ratio comparison of the actual and expected values determined in steps 307a and 307b. As a matter of convention, the eCIS is described herein as the actual blush area (307a) divided by the expected blush area (307b); however, the person of ordinary skill in the art will readily understand that the reciprocal ratio is equally valid.

Figure 4:
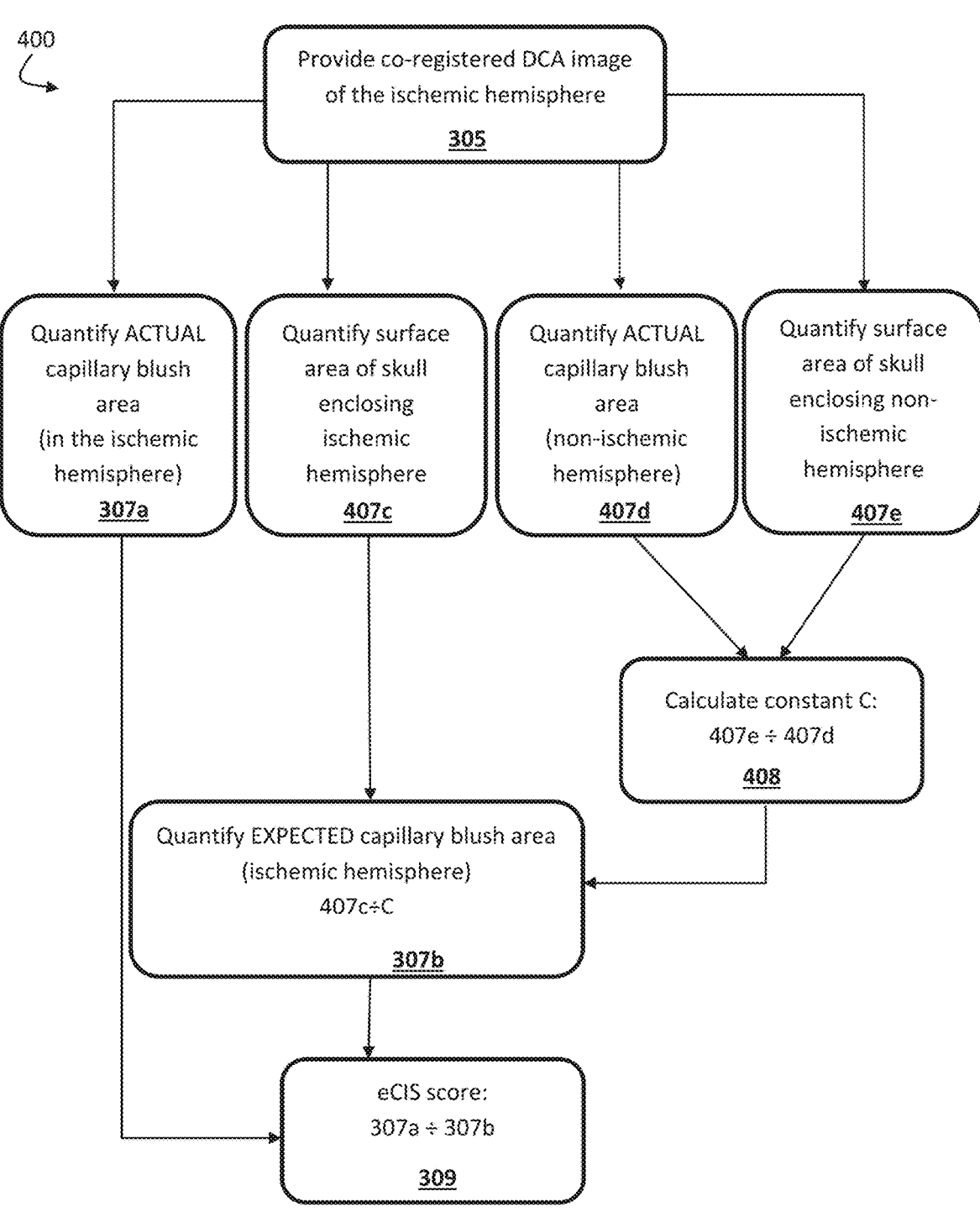
FIG. 4 is a diagram showing a first method for carrying out an embodiment.

FIG. 4 illustrates one specific methodology 400 for calculating the expected blush area noted in step 307b. This method 400 involves quantitatively determining the areas of four features of the DCA. In step 407c the surface area of the inside of the skull section enclosing the ischemic hemisphere is determined. In step 407d the actual capillary blush area of the non-ischemic hemisphere is determined, and in 407e the surface area of the inside of the skull section enclosing the non-ischemic hemisphere is also determined. This method 400 is based on the assumption that the surface area of a brain hemisphere is related to the surface area of the skull enclosing it by a multiplier, and that the multiplier is constant between hemispheres according to Eq. 1 and step 408 of FIG. 4. Furthermore, according to this embodiment, the surface area of a hemisphere is also assumed to be equal to the expected blush area of the same hemisphere in a healthy brain. That is, the entire surface of the hemisphere should exhibit capillary blush. Accordingly, the area-ratio of the non-ischemic hemisphere and the section of skull enclosing it, can be used to calculate the expected blush area of the ischemic hemisphere ($A_{Expected}$) according to Eq. 2. More specifically, the constant C is divided into the quantitatively determined area of the bony landmark (skull section) enclosing the ischemic hemisphere, yielding the expected area ($A_{Expected}$) i.e., the blush area that the ischemic hemisphere would have exhibited if it were healthy. Having estimated the expected area in step 307b, the eCIS can be calculated in step 309 as previously described.

Figure 5:
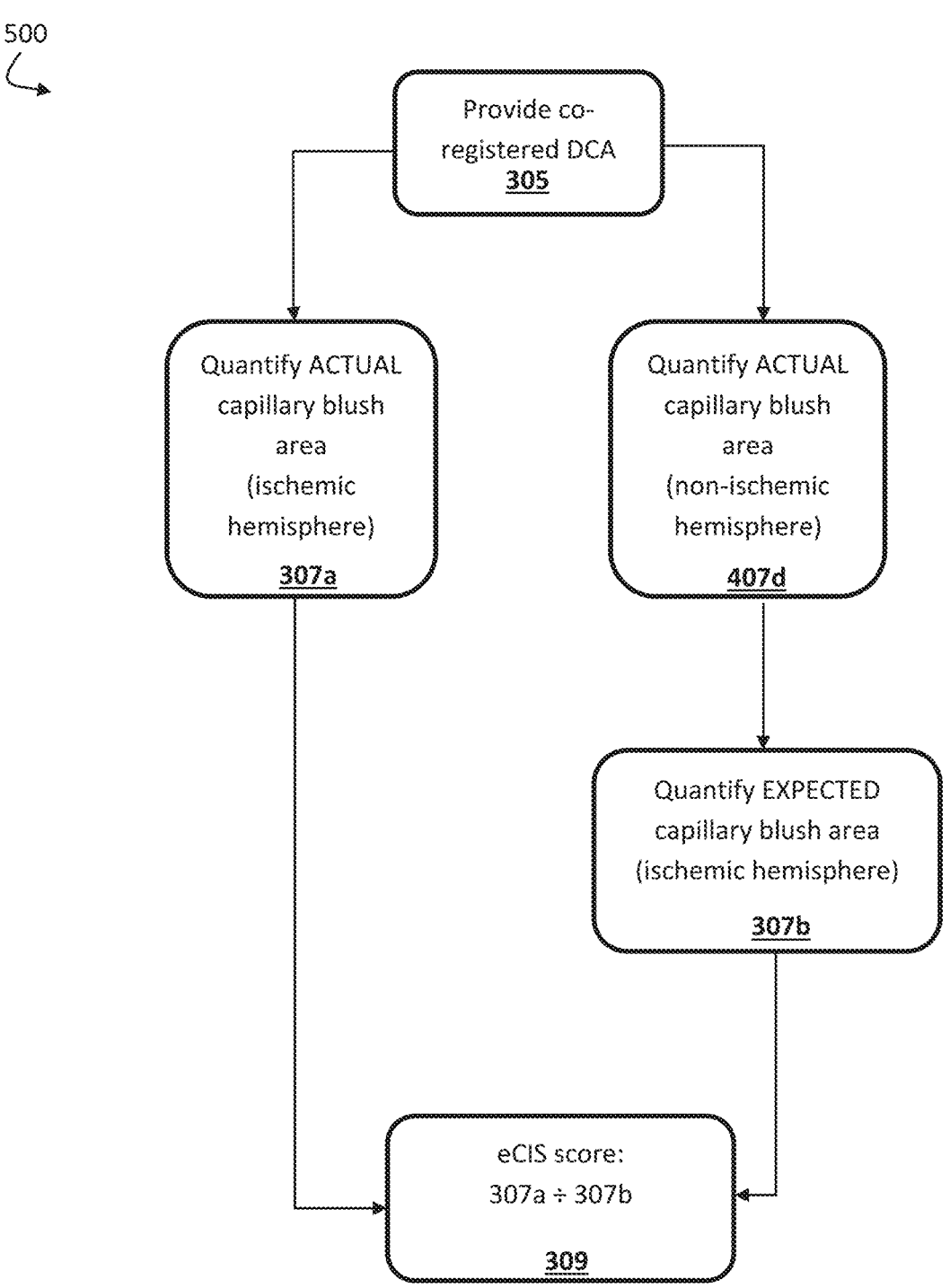
FIG. 5 is a diagram showing a second method for carrying out an embodiment.

FIG. 5 illustrates another method 500 for estimating the expected capillary blush area of the ischemic hemisphere ($A_{Expected}$). In this method, the two hemispheres of the same brain are assumed to have the same, or negligibly different, dimensions. Therefore, only two quantities are measured: the actual capillary blush area of the ischemic hemisphere (step 307a), and the actual capillary blush area of the non-ischemic hemisphere (step 407d). The latter quantity is assumed equal to, or negligibly different from, the expected capillary blush area of the ischemic hemisphere ($A_{Expected}$) in step 307b, and the eCIS is calculated in step 309 accordingly. Accordingly, in this embodiment 500 the step of quantifying the expected capillary blush area (307b) is to be interpreted as equating the actual capillary blush area of the non-ischemic hemisphere to the expected capillary blush are of the ischemic hemisphere. The act of equating, as used herein, means setting a variable equal to a selected quantity. For instance, with reference to FIG. 5, the act of equating the actual capillary blush area of the non-ischemic hemisphere to the expected capillary blush are of the ischemic hemisphere means setting the variable $A_{Expected}$ equal to the capillary blush area of the of the non-ischemic hemisphere as calculated according to methods described herein.

Figure 6:
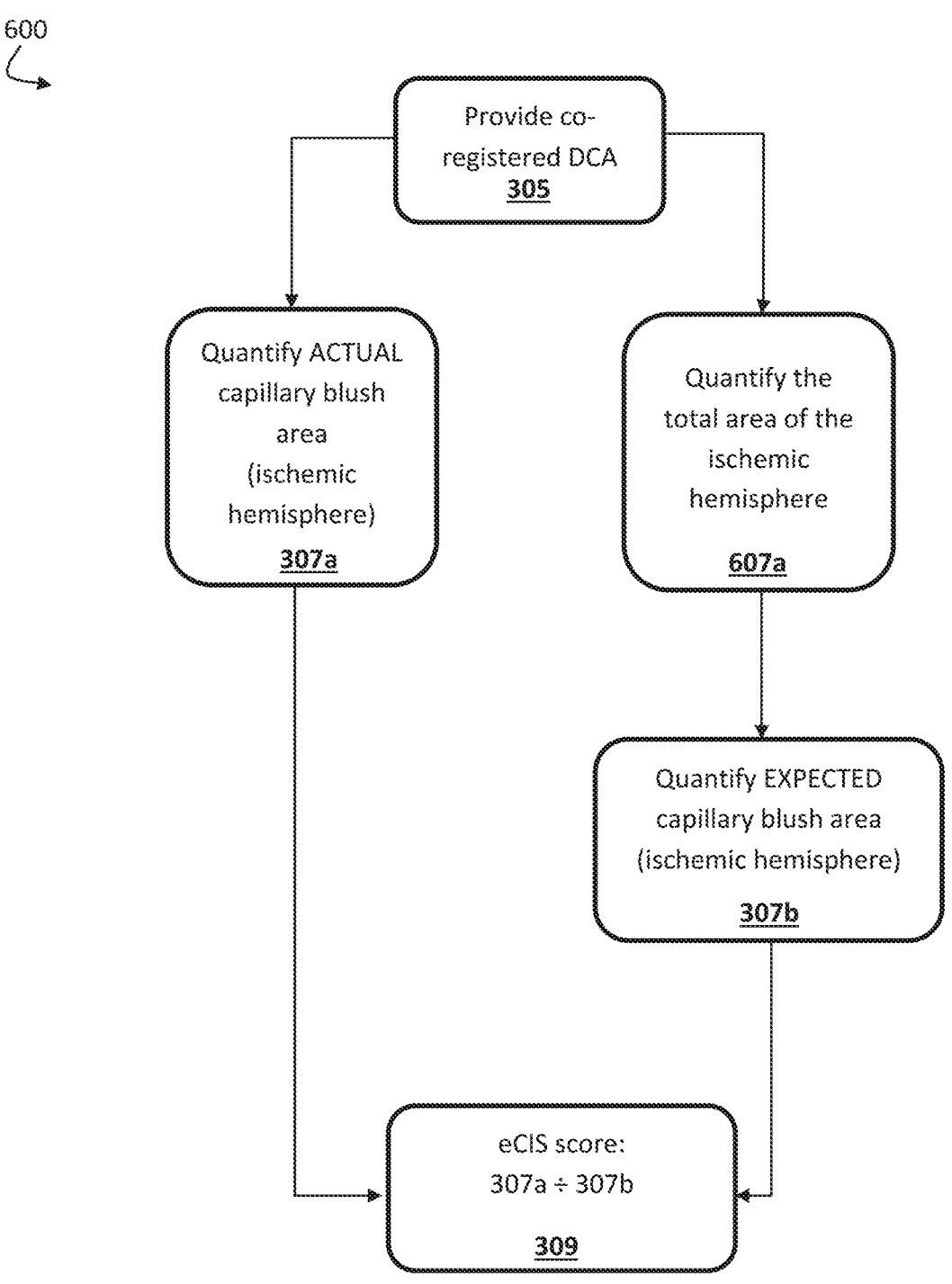
FIG. 6 is a diagram showing a third method for carrying out an embodiment.

FIG. 6 illustrates another method 600 for estimating the expected capillary blush area of the ischemic hemisphere (A$_{Expected}$). According to this method 600, only a DCA image of the ischemic hemisphere is required. The outline of the ischemic hemisphere is identified and the entire area of tissue bounded by the outline is assumed equal to, or negligibly different from, the expected capillary blush area of the ischemic hemisphere (A$_{Expected}$). According to this method 600, it may be advantageous to also recognize the outline of brain ventricles, which are void spaces, and either subtract the ventricle area from the total area within the hemisphere outline, or neglect the ventricles when otherwise quantitatively determining the area of tissue bounded by the hemisphere outline.

With particular regard to embodiments comprising artificial intelligence data models, a supervised learning method according to some embodiments of the invention includes the following. A plurality of de-identified DCA medical images may be obtained. The images may be obtained in digital form, or they may be obtained in hardcopy and then digitized. The images may be rendered in gray scale. According to some embodiments, the images are annotated and labeled to prepare them for a machine learning step. The annotation comprises drawing an outline around structures and features that the AI data model is to learn to recognize. A suitable label indicates a feature type e.g., a hemisphere outline, an area of capillary blush, an area of ischemia or infarction, and structures such as ventricle boundaries and skull sections. The person having ordinary skill will understand that labels need not be included as a feature perceptible by human vision. Rather, labels can be provided according to other known means, including in the form of computer-readable code. After annotating and labeling the image data, the data is provided to the AI data model according to well-known machine vision means.

Figure 7:
FIG. 7 is an example of an annotated DCA image suitable for a machine learning step of one embodiment, showing the partial capillary blush of an ischemic hemisphere.
Figure 8:
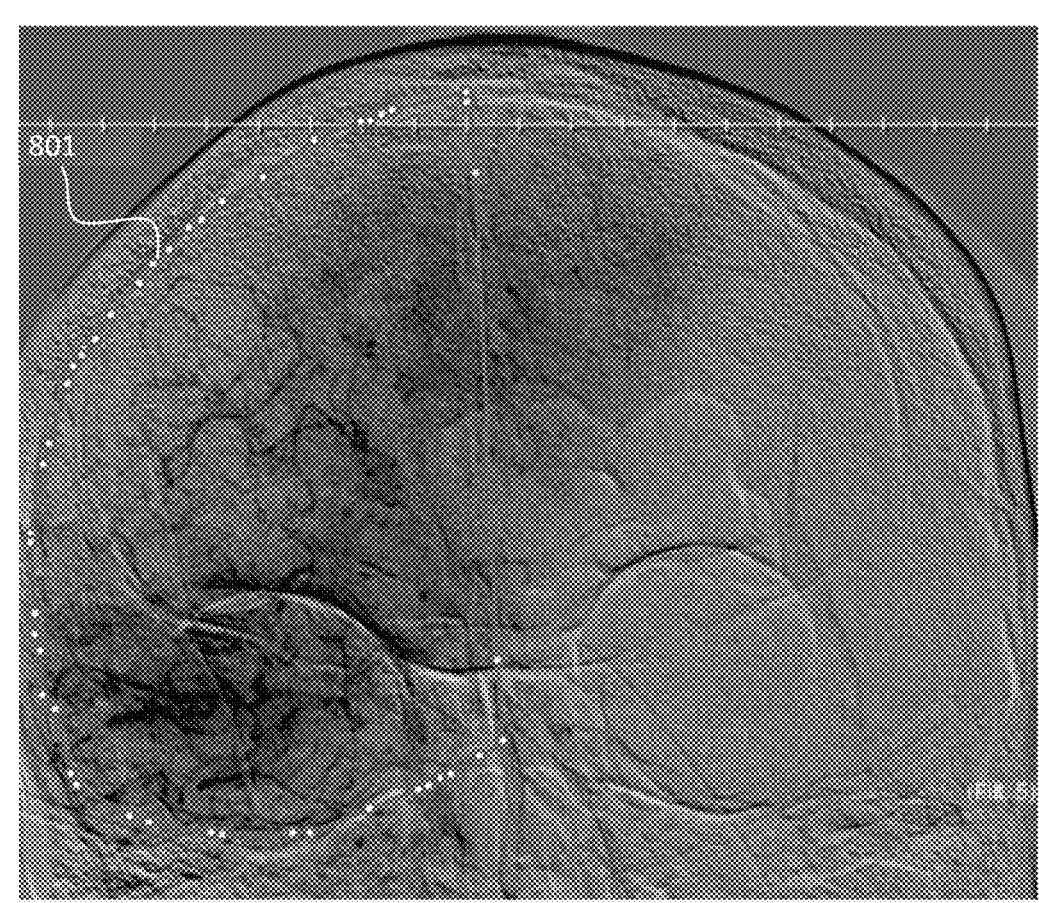
FIG. 8 is an example of an annotated DCA image suitable for a machine learning step of one embodiment, showing a skull annotation.
Figure 9:
FIG. 9 is an example of an annotated DCA image suitable for a machine learning step of one embodiment, showing capillary blush in a posterior portion of the brain due to a vertebral artery injection.
Figure 9:
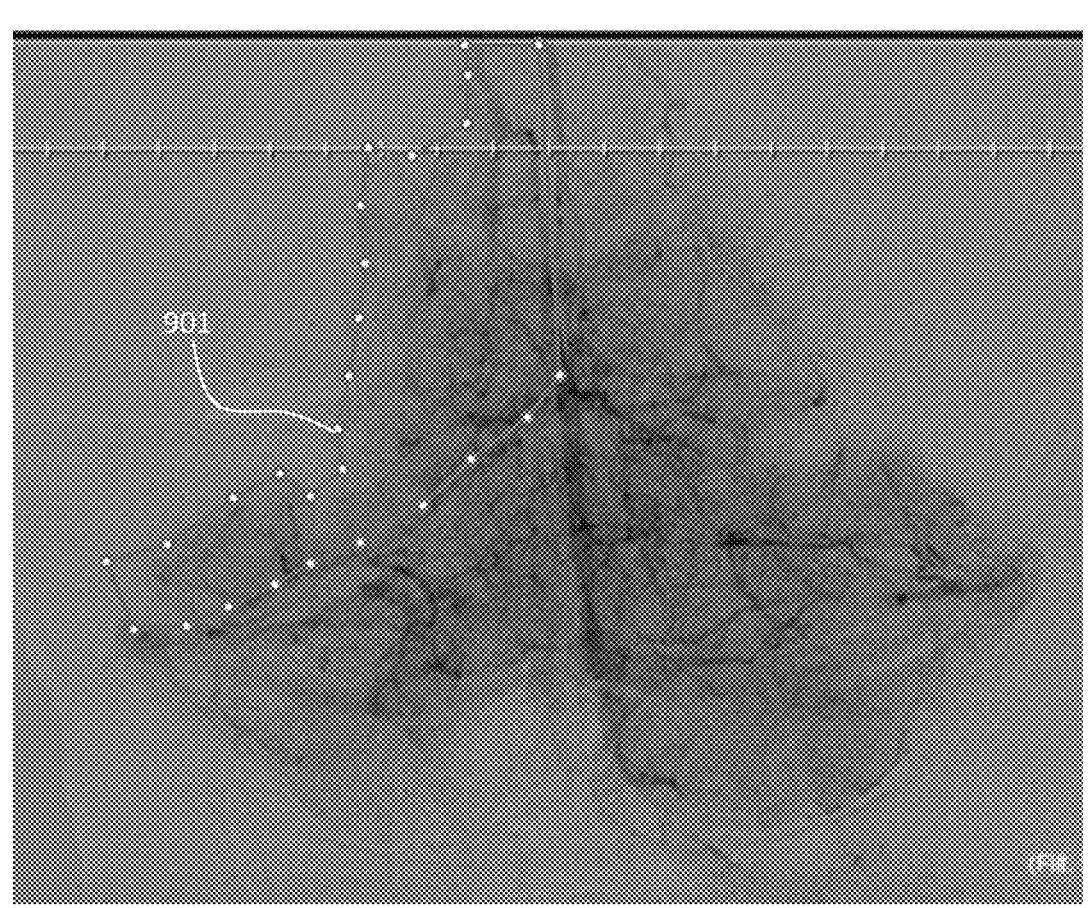
Figure 10:
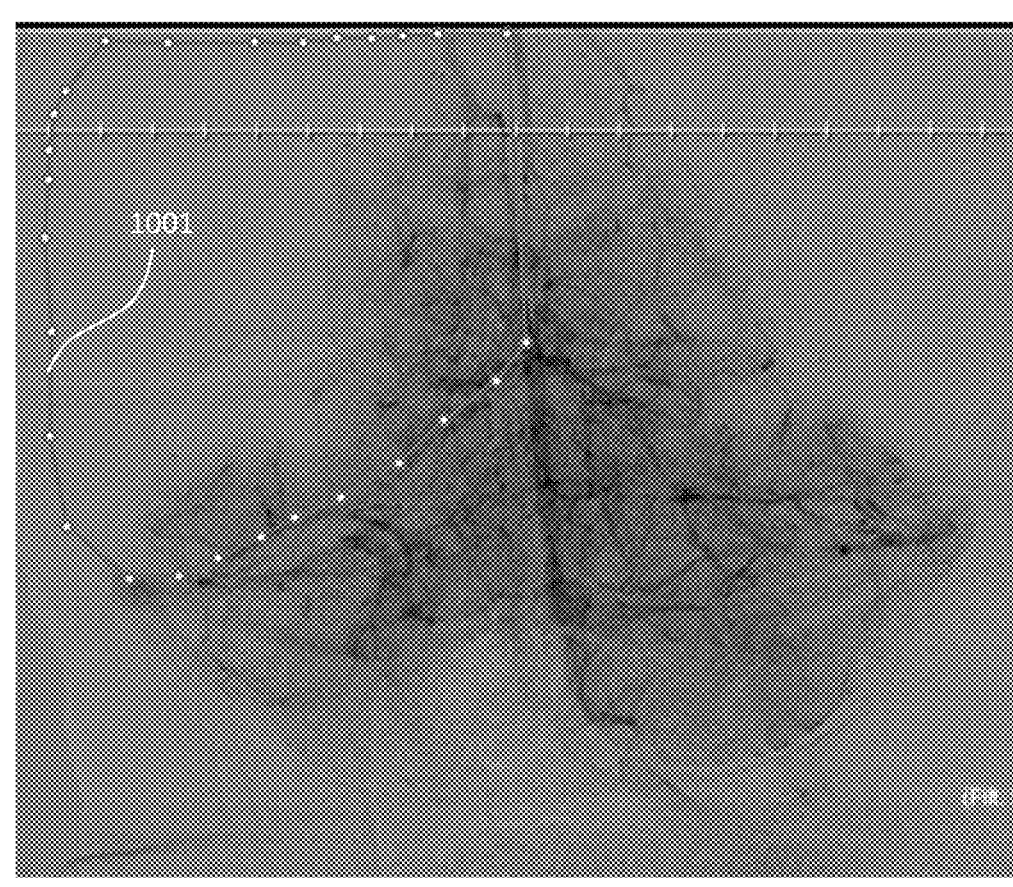
FIG. 10 is an example of an annotated DCA image suitable for a machine learning step of one embodiment, showing a skull annotation in relation to blush in the posterior brain.
Figure 11:
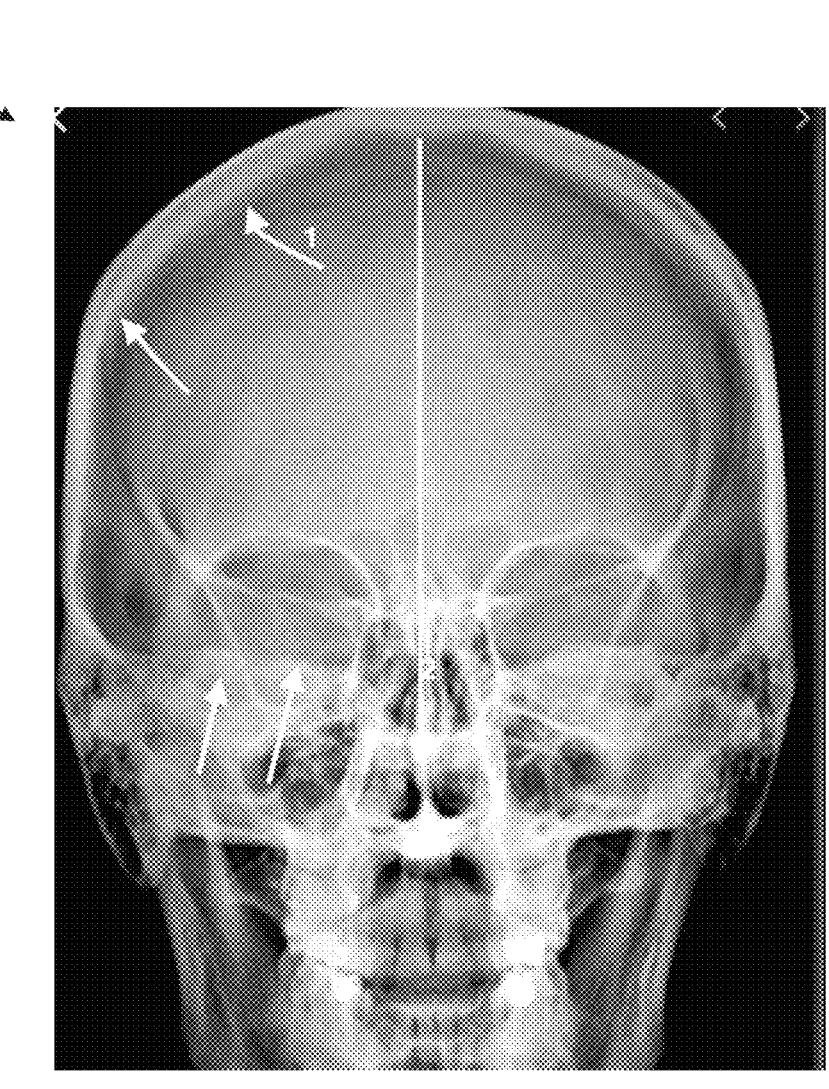
FIG. 11 is a frontal view x-ray image showing the bony landmark in high contrast.

FIG. 7 is an example 700 of an annotated DCA image showing an outline of the blush area 701 of an infarcted hemisphere. The outlined area 701 indicates the healthy brain tissue. FIG. 8 is an example 800 of annotations for teaching the AI data model to recognize the boundaries of the skull 801 for calculating the surface area of a section of skull. FIG. 9 is an example 900 of a DCA annotated 901 to show the blush area of a posterior portion of the brain. This portion of the brain was injected with contrast dye through a vertebral artery. FIG. 10 is an example 1000 of a DCA annotated 1001 to show the skull boundaries. In this example 1000, the posterior brain displays capillary blush due to a vertebral artery injection. FIG. 11 is an x-ray image of a skull in frontal view 1100. This image 1100 is not annotated for machine learning, and is not required by embodiments of the invention. Instead, it is provided as a convenience and for illustration. Arrows are provided, pointing to the boundaries of the skull used for calculating the surface area of the bony landmark.

Figure 12:
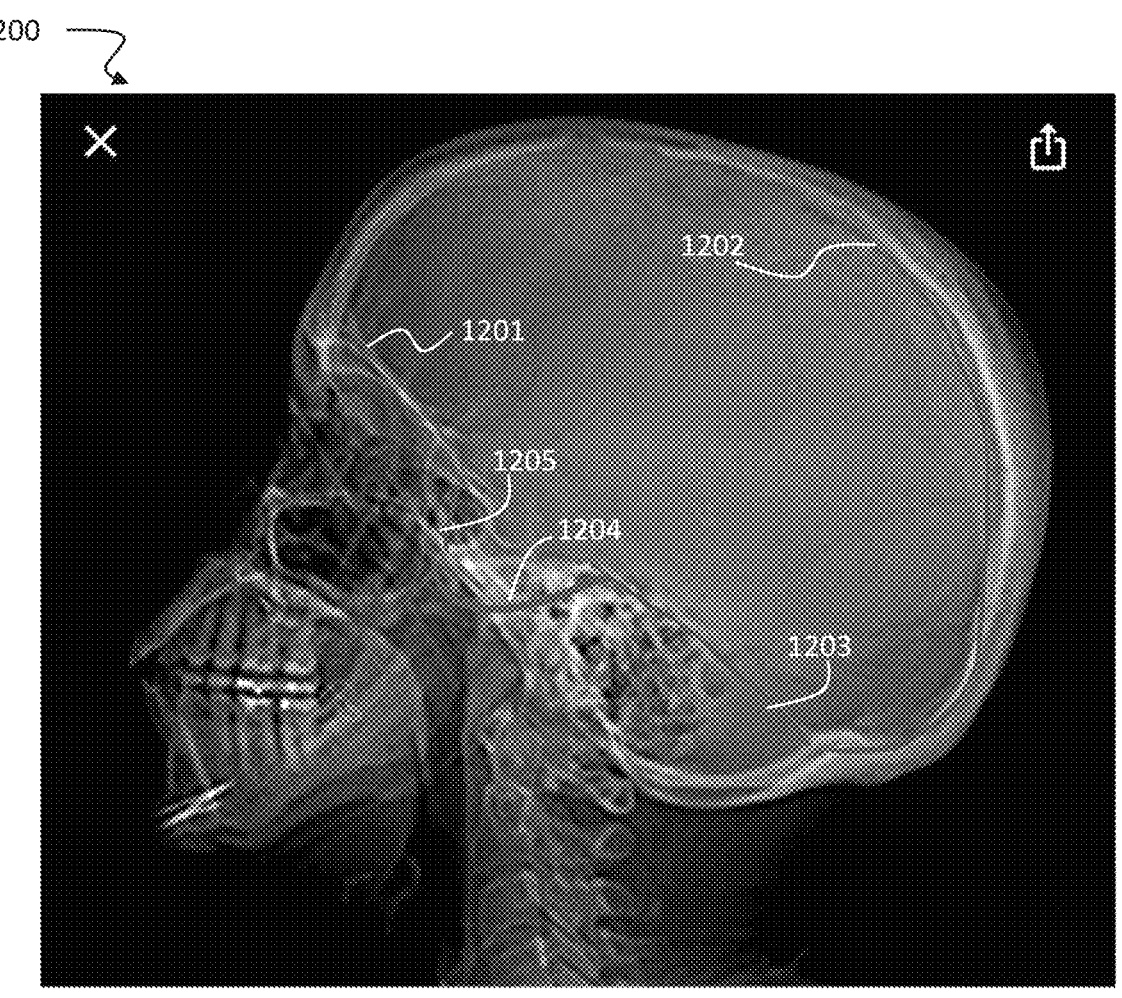
FIG. 12 is a lateral view x-ray image showing the bony landmark in high contrast.
Figure 13:
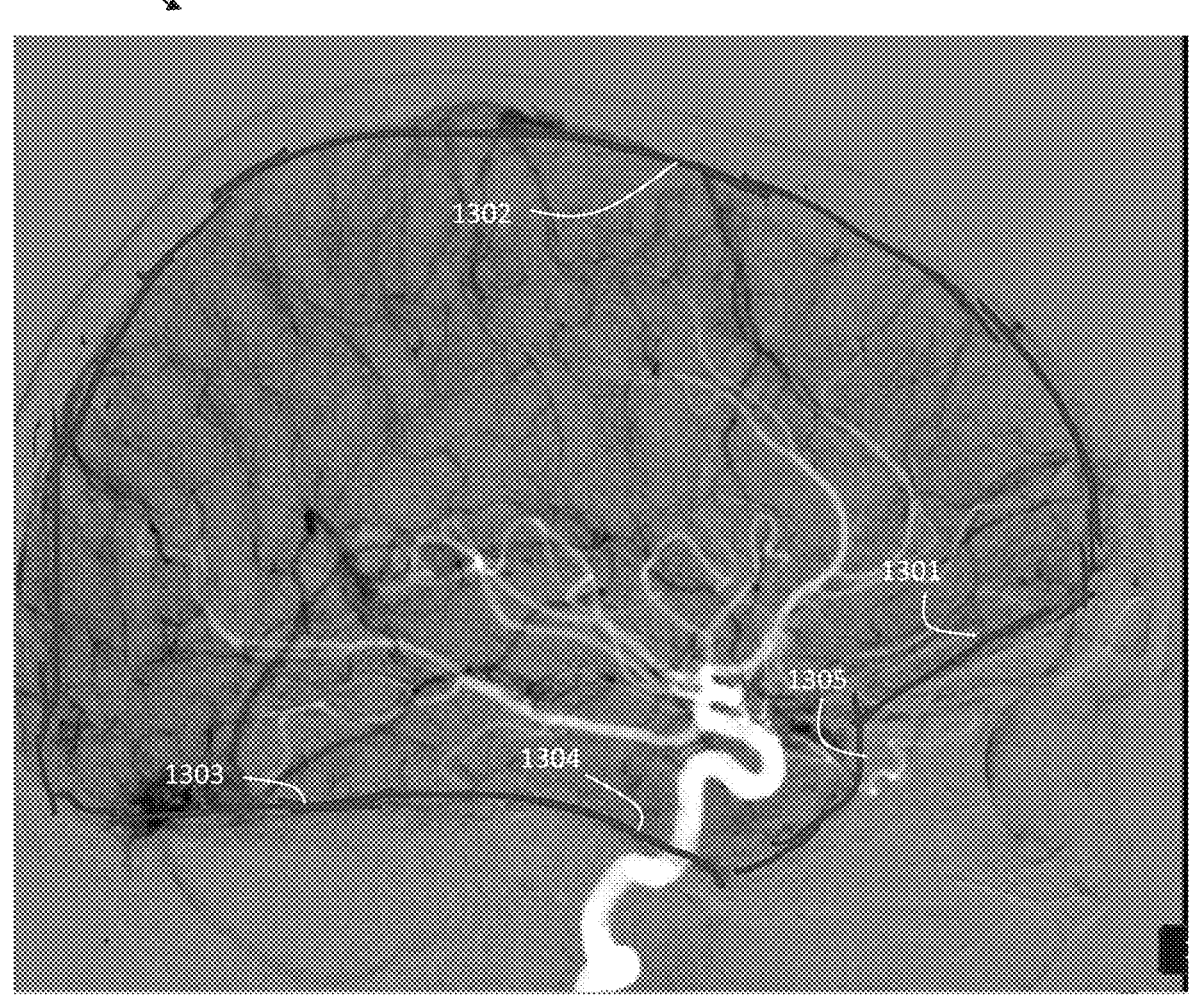
FIG. 13 is an example of a lateral DCA image with the blush area annotated.

Turning to FIGS. 12 and 13, these figures are examples 1200, 1300 of DCA lateral views that can be used to calculate an eCIS according to methods described herein. The principal difference between calculating an eCIS score from a lateral view as opposed to a frontal view is in the image annotations e.g., for training an AI data model. With reference to FIG. 12, lines 1201 through 1205 demarcate the skull boundaries. Similar to a frontal view, the area within the skull boundaries is used to calculate the areas of the bony landmarks according to the methods of Equations 1 through 3. For example, line 1201 follows the sphenoid bone behind the eyes, line 1202 follows the cranium along the inner bony table to the level of the greater trochanter. Lines 1203 and

1204 run from the greater trochanter to the Internal Acoustic Meatus (IAM) lying on the top of the mastoid air cells. A semicircle starts at the IAM indicated by line 1204, and arcs through line 1205 reaching the posterior edge of line 1201. This outline is suitable for training an AI data model to recognize the skull boundaries for purposes of carrying the eCIS methods of the invention on a lateral DCA image. A similar set of lines is shown in FIG. 13 where lines 1301 through 1305 demarcate the boundaries of the blush area. Since FIG. 13 is a DCA of a non-ischemic hemisphere, lines 1301 through 1305 closely correspond to lines 1201 through 1205.

Having described the methods of quantifying, calculating, and/or estimating an expected capillary blush area (step 307*b*) of DCA frontal views, the person having ordinary skill in the art will be readily capable of extending the principles already taught to lateral views. Accordingly, suitable methodologies for carrying out step 307*b* include those which are illustrated and described with reference to FIGS. 4, 5, and 6. For instance, with reference to FIG. 4, the areas of the non-ischemic hemisphere and the boney landmark enclosing it can be determined and used to calculate the constant C according to Equation 1. The expected capillary blush area of ischemic hemisphere can then be calculated by dividing C into the area of the section of skull enclosing the ischemic hemisphere. With reference to FIG. 5, the expected capillary blush area of the ischemic hemisphere is assumed equal to the actual blush area of the non-ischemic hemisphere. And, with reference to FIG. 6, the expected capillary blush area of the ischemic hemisphere is assumed equal to the area bounding the entire ischemic hemisphere, minus the ventricles and any other structures that do not blush in a non-ischemic hemisphere.

The data model is suitably coded to integrate the provided data and recognize patterns therein, which it can later use to recognize similar structures in new data having no annotations or labels. An AI data model according to an embodiment of the invention may, for instance, recognize an ischemic region of brain tissue including the boundaries thereof, and may similarly recognize non-ischemic areas and boundaries. The data model, having established the boundaries, may calculate the area within the boundaries. This is also referred to herein as the act of quantitatively determining, or simply determining. The person having ordinary skill in the art will understand that the data model need not handle the area calculation, as this may be addressed according to known computing methods not involving AI, and not requiring the additional data model training necessary to make such calculation. Thus, in some embodiments, the AI data model recognizes and marks the boundaries of features, while their areas are calculated with reference to the markings, but by means other than artificial intelligence.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

I claim:

1. A capillary index scoring method, comprising the steps of:

providing a co-registered diagnostic cerebral angiogram in frontal view or lateral view;

quantifying an actual capillary blush area of a portion of the diagnostic cerebral angiogram representing an ischemic hemisphere, wherein the step of quantifying an actual capillary blush area comprises recognizing boundaries of an ischemic region of the ischemic hemisphere, and calculating the actual capillary blush area within the boundaries;

quantifying an expected capillary blush area of the portion of the diagnostic cerebral angiogram representing the ischemic hemisphere, wherein the step of quantifying an expected capillary blush area comprises recognizing boundaries of an bony landmark of the ischemic hemisphere, calculating a surface area withing the boundaries of the bony landmark of the ischemic hemisphere, and dividing the area within the boundaries of the bony landmark of the ischemic hemisphere by a constant relating the area within the boundaries of the bony landmark of the ischemic hemisphere to an area of a non-ischemic hemisphere; and dividing the quantified actual capillary blush area by the quantified expected capillary blush area.

2. The method of claim 1, wherein the diagnostic cerebral angiogram is a frontal view.

3. The method of claim 2, wherein the step of providing the co-registered diagnostic cerebral angiogram comprises the steps of:

administering a first injection of a contrast dye to a carotid artery branch feeding the ischemic hemisphere;

administering a second injection of the contrast dye to a carotid artery branch feeding a non-ischemic hemisphere;

administering a third injection of the contrast dye to a vertebral artery branch feeding a posterior brain portion; and capturing a co-registered two-dimensional x-ray projection image of the ischemic hemisphere, and the non-ischemic hemisphere.

4. The method of claim 3, wherein the step of capturing the co-registered two-dimensional x-ray projection image includes one or more of a projection image of an interior surface of a skull section enclosing the ischemic hemisphere, or a projection image of an interior surface of a skull section enclosing the non-ischemic hemisphere.

5. The method of claim 4, further comprising the steps of:

quantifying an actual capillary blush area of the portion of the diagnostic cerebral angiogram representing the interior surface of the skull section enclosing the non-ischemic hemisphere; and quantifying an actual capillary blush area of the portion of the diagnostic cerebral angiogram representing the non-ischemic hemisphere.

6. The method of claim 5, wherein the step of quantifying an expected capillary blush area of the portion of the diagnostic cerebral angiogram representing the ischemic hemisphere, comprises the step of:

dividing the actual capillary blush area of the portion of the diagnostic cerebral angiogram representing the ischemic hemisphere by a ratio of:

(a) a numerator consisting of the actual capillary blush area of the portion of the diagnostic cerebral angiogram representing the interior surface of the skull section enclosing the non-ischemic hemisphere; and (b) a denominator consisting of the actual capillary blush area of the portion of the diagnostic cerebral angiogram representing the non-ischemic hemisphere.

7. The method of claim 3, wherein the step of quantifying the expected capillary blush area of the portion of the diagnostic cerebral angiogram representing the ischemic hemisphere comprises the steps of:

quantifying an actual capillary blush area of the portion of the diagnostic cerebral angiogram representing a non-ischemic hemisphere; and equating the actual capillary blush area of the portion of the diagnostic cerebral angiogram representing a non-ischemic hemisphere to the expected capillary blush area of the diagnostic cerebral angiogram representing the ischemic hemisphere.

8. The method of claim 3, wherein the step of quantifying the expected capillary blush area of the portion of the diagnostic cerebral angiogram representing the ischemic hemisphere comprises the steps of:

identifying an outline of the ischemic hemisphere;

calculating an area of tissue bounded by the outline of the ischemic hemisphere; and equating the area bounded by the outline of the ischemic hemisphere to the expected capillary blush area of the portion of the diagnostic cerebral angiogram representing the ischemic hemisphere.

9. The method of claim 3, wherein the step of quantifying the expected capillary blush area of the portion of the diagnostic cerebral angiogram representing the ischemic hemisphere comprises the steps of:

identifying an outline of the ischemic hemisphere;

calculating an area bounded by the outline of the ischemic hemisphere;

identifying an outline of a ventricle;

calculating an area bounded by the outline of the ventricle; and equating the difference between the area of the ventricle and the area of the ischemic hemisphere to the expected capillary blush area of the portion of the diagnostic cerebral angiogram representing the ischemic hemisphere.

10. The method of claim 3, wherein the step of capturing the co-registered two-dimensional x-ray projection image includes one or more of a projection image of an interior surface of a skull section enclosing the ischemic hemisphere, or a projection image of an interior surface of a skull section enclosing the non-ischemic hemisphere.

11. The method of claim 10, further comprising the steps of:

quantifying an actual capillary blush area of the portion of the diagnostic cerebral angiogram representing the interior surface of the skull section enclosing the non-ischemic hemisphere; and quantifying an actual capillary blush area of the portion of the diagnostic cerebral angiogram representing the non-ischemic hemisphere.

12. The method of claim 11, wherein the step of quantifying an expected capillary blush area of the portion of the diagnostic cerebral angiogram representing the ischemic hemisphere, comprises the step of:

dividing the actual capillary blush area of the portion of the diagnostic cerebral angiogram representing the ischemic hemisphere by a ratio of:

(a) a numerator consisting of the actual capillary blush area of the portion of the diagnostic cerebral angiogram representing the interior surface of the skull section enclosing the non-ischemic hemisphere; and (b) a denominator consisting of the actual capillary blush area of the portion of the diagnostic cerebral angiogram representing the non-ischemic hemisphere.

13. The method of claim 1, wherein the step of quantifying the actual capillary blush area of the portion of the diagnostic cerebral angiogram representing the ischemic hemisphere includes the steps of:

annotating a plurality of diagnostic cerebral angiograms of healthy brains and ischemic brains, the annotations indicating ischemic brain tissue areas having no capillary blush, and healthy brain tissue areas having normal capillary blush;

training an artificial intelligence data model using the annotated plurality of diagnostic cerebral angiograms of healthy and ischemic brains to recognize ischemic brain tissue areas having no capillary blush, and to recognize non-ischemic brain tissue areas having normal capillary blush;

the artificial intelligence data model recognizing the actual capillary blush area of the portion of the diagnostic cerebral angiogram representing the ischemic hemisphere; and quantifying the recognized actual capillary blush area of the portion of the diagnostic cerebral angiogram representing the ischemic hemisphere.

14. The method of claim 1, wherein the step of quantifying an expected capillary blush area of the portion of the diagnostic cerebral angiogram representing an ischemic hemisphere includes the step of:

annotating a plurality of diagnostic cerebral angiograms of healthy brains and ischemic brains, the annotations indicating ischemic brain tissue areas having no capillary blush, and healthy brain tissue areas having normal capillary blush, and the annotations further indicating anatomical structures including an interior surface of a skull section enclosing the ischemic hemisphere, and an interior surface of a skull section enclosing the non-ischemic hemisphere;

training an artificial intelligence data model using the annotated plurality of diagnostic cerebral angiograms of healthy brains and ischemic brains to recognize non-ischemic brain tissue areas having normal capillary blush, an interior surface of a skull section enclosing the ischemic hemisphere, and an interior surface of a skull section enclosing the non-ischemic hemisphere;

the artificial intelligence data model recognizing a non-ischemic brain tissue area having normal capillary blush, an interior surface of a skull section enclosing the non-ischemic hemisphere, and an interior surface of a skull section enclosing the ischemic hemisphere;

quantifying the areas of the recognized non-ischemic brain tissue area having normal capillary blush, the interior surface of the skull section enclosing the non-ischemic hemisphere, and the interior surface of a skull section enclosing the ischemic hemisphere;

calculating a constant C, equal to the quantified area the skull section enclosing the non-ischemic hemisphere divided by the quantified area of the non-ischemic brain tissue area having normal capillary blush; and calculating the expected capillary blush area of the portion of the diagnostic cerebral angiogram representing the ischemic hemisphere, equal to the quantified area of the interior surface of a skull section enclosing the ischemic hemisphere divided by the constant C.

15. The method of claim 1, wherein the step of quantifying an expected capillary blush area of the portion of the diagnostic cerebral angiogram representing an ischemic hemisphere includes the step of:

annotating a plurality of diagnostic cerebral angiograms of healthy brains and ischemic brains, the annotations indicating ischemic brain tissue areas having no capillary blush, and healthy brain tissue areas having normal capillary blush;

training an artificial intelligence data model using the annotated plurality of diagnostic cerebral angiograms of healthy brains and ischemic brains to recognize ischemic brain tissue areas having no capillary blush, and to recognize non-ischemic brain tissue areas having normal capillary blush;

the artificial intelligence data model recognizing the actual capillary blush area of the portion of the diagnostic cerebral angiogram representing the non-ischemic hemisphere;

quantifying the area of actual capillary blush of the portion of the diagnostic cerebral angiogram representing the non-ischemic hemisphere; and equating the area of actual capillary blush of the portion of the diagnostic cerebral angiogram representing the non-ischemic hemisphere to the expected capillary blush area of the portion of the diagnostic cerebral angiogram representing the ischemic hemisphere.

16. The method of claim 1, wherein the step of quantifying an expected capillary blush area of the portion of the diagnostic cerebral angiogram representing an ischemic hemisphere includes the step of:

annotating a plurality of diagnostic cerebral angiograms of healthy brains and ischemic brains, the annotations indicating ischemic brain tissue areas having no capillary blush, healthy brain tissue areas having normal capillary blush, and further indicating peripheral boundaries of brain hemispheres;

training an artificial intelligence data model using the annotated plurality of diagnostic cerebral angiograms of healthy brains and ischemic brains to recognize ischemic brain tissue areas having no capillary blush, and to recognize non-ischemic brain tissue areas having normal capillary blush, and to recognize peripheral boundaries of brain hemispheres;

the artificial intelligence data model recognizing the actual capillary blush area of the portion of the diagnostic cerebral angiogram representing the ischemic hemisphere, and the artificial intelligence data model recognizing a peripheral boundary of the ischemic hemisphere in the portion of the diagnostic cerebral angiogram representing the ischemic hemisphere;

quantifying the area of actual capillary blush of the portion of the diagnostic cerebral angiogram representing the ischemic hemisphere, and quantifying an area bounded by the peripheral boundary of the ischemic hemisphere in the portion of the diagnostic cerebral angiogram representing the ischemic hemisphere; and equating the area bounded by the peripheral boundary of the ischemic hemisphere in the portion of the diagnostic cerebral angiogram representing the ischemic hemisphere to the expected capillary blush area of the portion of the diagnostic cerebral angiogram representing the ischemic hemisphere.

17. The method of claim 16, further comprising the steps of:

annotating the plurality of diagnostic cerebral angiograms of healthy brains and ischemic brains, the annotations indicating ventricles;

training the artificial intelligence data model using the annotated plurality of diagnostic cerebral angiograms of healthy brains and ischemic brains to recognize ventricles;

the artificial intelligence data model recognizing a ventricle in the portion of the diagnostic cerebral angiogram representing the ischemic hemisphere; and quantifying the area of the recognized ventricle in the portion of the diagnostic cerebral angiogram representing the ischemic hemisphere;

wherein the step of equating further comprises subtracting the area of the recognized ventricle in the portion of the diagnostic cerebral angiogram representing the ischemic hemisphere from the area bounded by the peripheral boundary of the ischemic hemisphere, and setting the difference equal to the expected capillary blush area of the portion of the diagnostic cerebral angiogram representing the ischemic hemisphere.

18. The method of claim 17, further comprising the step of distinguishing the ventricle from ischemic brain tissue.

19. The method of claim 1, wherein the step of quantifying the expected capillary blush area of the portion of the diagnostic cerebral angiogram representing the ischemic hemisphere comprises the steps of:

quantifying an actual capillary blush area of the portion of the diagnostic cerebral angiogram representing a non-ischemic hemisphere; and equating the actual capillary blush area of the portion of the diagnostic cerebral angiogram representing a non-ischemic hemisphere to the expected capillary blush area of the diagnostic cerebral angiogram representing the ischemic hemisphere.

20. The method of claim 1, wherein the step of quantifying the expected capillary blush area of the portion of the diagnostic cerebral angiogram representing the ischemic hemisphere comprises the steps of:

identifying an outline of the ischemic hemisphere;

calculating an area of tissue bounded by the outline of the ischemic hemisphere; and equating the area bounded by the outline of the ischemic hemisphere to the expected capillary blush area of the portion of the diagnostic cerebral angiogram representing the ischemic hemisphere.

* * * * *